(12) United States Patent
Briese et al.

(10) Patent No.: US 10,156,515 B2
(45) Date of Patent: Dec. 18, 2018

(54) MATERIAL DETECTION SYSTEM

(71) Applicant: GED Integrated Solutions, Inc., Twinsburg, OH (US)

(72) Inventors: William A. Briese, Hinckley, OH (US); Clifford J. Weber, Richfield, OH (US); Steven W. Pesek, Hinckley, OH (US)

(73) Assignee: GED Integrated Solutions, Inc., Twinsburg, OH (US)

( * ) Notice: Subject to any disclaimer, the term of this patent is extended or adjusted under 35 U.S.C. 154(b) by 0 days.

(21) Appl. No.: 15/405,954

(22) Filed: Jan. 13, 2017

(65) Prior Publication Data

US 2017/0205334 A1 Jul. 20, 2017

Related U.S. Application Data

(60) Provisional application No. 62/278,701, filed on Jan. 14, 2016.

(51) Int. Cl.
| | |
|---|---|
| *G01N 21/25* | (2006.01) |
| *G01N 21/47* | (2006.01) |
| *G01N 33/20* | (2006.01) |
| *G01J 3/46* | (2006.01) |
| *G01N 21/86* | (2006.01) |
| *G01V 3/10* | (2006.01) |

(52) U.S. Cl.
CPC .............. *G01N 21/25* (2013.01); *G01J 3/46* (2013.01); *G01N 21/251* (2013.01); *G01N 21/474* (2013.01); *G01N 21/86* (2013.01); *G01N 33/20* (2013.01); *G01V 3/10* (2013.01); *G01N 2021/8609* (2013.01)

(58) Field of Classification Search
None
See application file for complete search history.

(56) References Cited

U.S. PATENT DOCUMENTS

| | | |
|---|---|---|
| 3,889,503 A | 6/1975 | Luenser |
| 4,400,850 A | 8/1983 | Burnett |
| 5,351,476 A | 11/1994 | Leopold |
| 6,060,677 A | 5/2000 | Ulrichsen et al. |
| 7,448,246 B2 | 11/2008 | Briese et al. |
| 7,610,681 B2 | 11/2009 | Calcei et al. |
| 9,212,515 B2 | 12/2015 | Calcei et al. |
| 2007/0262000 A1* | 11/2007 | Valerio ................. B07C 5/344 209/556 |
| 2010/0224537 A1* | 9/2010 | Valerio ................. B07C 5/344 209/571 |
| 2013/0134243 A1 | 5/2013 | Leshem et al. |
| 2014/0260491 A1 | 9/2014 | Briese et al. |

* cited by examiner

*Primary Examiner* — Shawn Decenzo
(74) *Attorney, Agent, or Firm* — John A. Yirga, Esq.; Tarolli, Sundheim, Covell & Tummino LLP

(57) ABSTRACT

A system and method that automatically determine a type of material at a machine input to prevent damage to the machine. A user interface receives a selection of a material type to be loaded into the machine. A controller performs a safety check before starting a process using the machine by matching the selected material type to a material type at the machine input determined based on signals received from a plurality of sensors. The plurality of sensors comprise a material present sensor, a material type sensor opposed by a different material having a inductive sensor correction factor of 0.5 or less, and a material color sensor.

20 Claims, 11 Drawing Sheets

MATERIAL DETECTION SYSTEM

CROSS-REFERENCE TO RELATED APPLICATIONS

The present application claims priority to U.S. Provisional Patent Application Ser. No. 62/278,701 filed Jan. 14, 2016 entitled MATERIAL DETECTION SYSTEM; the entire contents of the above-identified application is incorporated herein by reference in its entirety for all purposes.

FIELD OF THE DISCLOSURE

The present disclosure relates to a material detection system and more specifically to a control method that uses the material detection system to determine a type of material at a machine input to prevent damage to the machine and/or allow for changes to occur to the machine or subsequent equipment based on the determination.

BACKGROUND

Insulating glass units (IGUs) are used in windows to reduce heat loss from building interiors during cold weather. IGUs are typically formed by a spacer assembly sandwiched between glass lites. The spacer assembly usually comprises a frame structure extending peripherally about the unit, a sealant material adhered both to the glass lites and the frame structure, and a desiccant for absorbing atmospheric moisture within the unit. The margins or the glass lites are flush with or extend slightly outwardly from the spacer assembly. The sealant extends continuously about the frame structure periphery and its opposite sides so that the space within the IGUs is hermetic.

U.S. Pat. No. 5,361,476 to Leopold discloses a method and apparatus for making IGUs wherein a thin flat strip of sheet material is continuously formed into a channel shaped spacer frame having corner structures and end structures, the spacer thus formed is cut off, sealant and desiccant are applied and the assemblage is bent to form a spacer assembly. The '476 patent is incorporated herein by reference.

U.S. Pat. No. 7,610,681 to Calcei et al. concerns spacer frame manufacturing equipment wherein a stock supply station includes a number of rotatable sheet stock coils, an indexing mechanism for positioning one of the coils and an uncoiling mechanism. Multiple other processing stations act on the elongated strip of sheet stock uncoiled from the stock supply station. The '681 patent is incorporated herein by reference.

U.S. Pat. No. 7,448,246 to Briese et al. concerns another spacer frame manufacturing system. As discussed in the '246 patent, spacer frames depicted are initially formed as a continuous straight channel constructed from a thin ribbon of stainless steel material e.g., 304 stainless steel having a thickness of 0.006-0.010 inches. As noted, other materials such as galvanized, tin plated steel, or aluminum can be used to construct the spacer frame. The '246 patent to Briese et al. is also incorporated herein by reference. Typical thickness for these other materials range from 0.006 to 0.025 inches in thickness.

U.S. Patent Publication No. 2014/0260491 entitled Automated Spacer Frame and Fabrication that published on Sep. 18, 2014 and is assigned to the assignee of the present application teaches, inter alia, stop assemblies that require changing based on the type of material being used to form a spacer frame from a supply station. The above-identified '491 publication is incorporated herein by reference.

SUMMARY

One aspect of the present disclosure comprises a system including a material detection system to detect a presence of a material during use at an input to a machine and to detect properties of the material. The material detection system includes a material present sensor, a material type sensor opposed by a different material having an inductive sensor correction factor of 0.5 or less, and a material color sensor. The system further comprises a controller of the machine to adjust at least one parameter of the machine based on a type of the material determined based on the properties of the material to prevent damage to the machine.

Another aspect of the present disclosure comprises a method of detecting a type and grade of material to be processed by a machine. The method includes the steps of providing a material present sensor, a material type sensor opposed by a different material having an inductive sensor correction factor of 0.5 or less, and providing a material color sensor. The method further includes providing a controller in the machine having a feedback loop to adjust at least one parameter of the machine based in the type of material determined.

Another aspect of the present disclosure comprises a system including a material detection system to detect a presence of a material during use at an input to a machine and to detect properties of the material. The material detection system includes a material present sensor comprising an inductive proximity sensor, a material type sensor opposed by a different material having an inductive sensor correction factor of 0.5 or less, wherein the material type sensor detects a portion of a magnetic field not absorbed by the material, and a material color sensor comprising a diffuse reflective photoelectric sensor that determines at least one of a degree of absorbency and reflectivity of the material. The system further includes a controller of the machine that includes a feedback loop to the machine, which performs a safety check matching a selected material type to a material type determined based on signals received from the sensors and based upon a prior and different material processed by said machine during use and adjusts at least one parameter of the machine based on a type of a subsequent material determined based on the properties of the subsequent material to prevent damage to the machine.

BRIEF DESCRIPTION OF THE SEVERAL VIEWS OF THE DRAWINGS

The foregoing and other features and advantages of the present disclosure will become apparent to one skilled in the art to which the present disclosure relates upon consideration of the following description of the disclosure with reference to the accompanying drawings, wherein like reference numerals, unless otherwise described refer to like parts throughout the drawings and in which.

Figure 1:
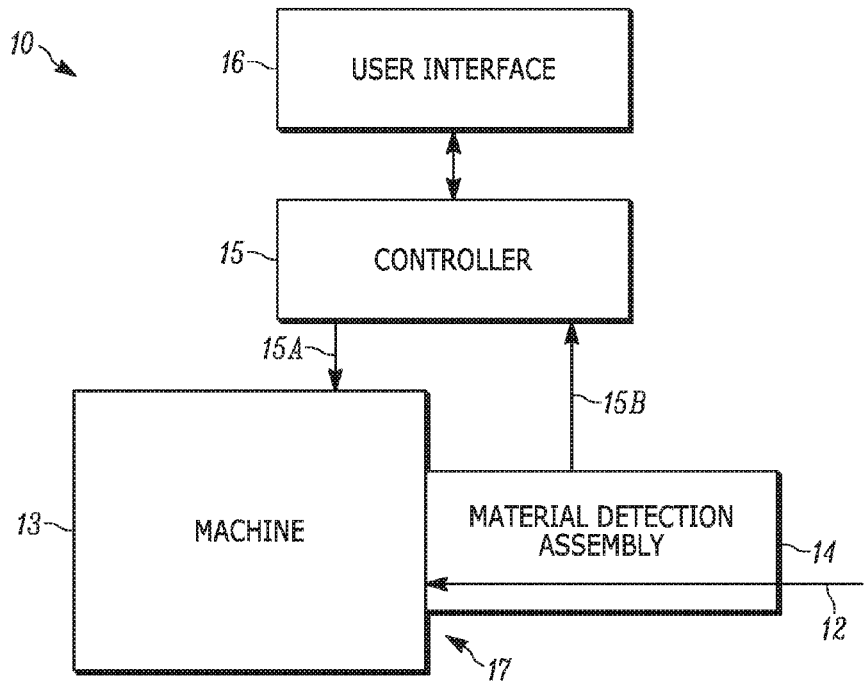
FIG. 1 is a block diagram of a material detection system constructed in accordance with one example embodiment of the present disclosure.
Figure 2:
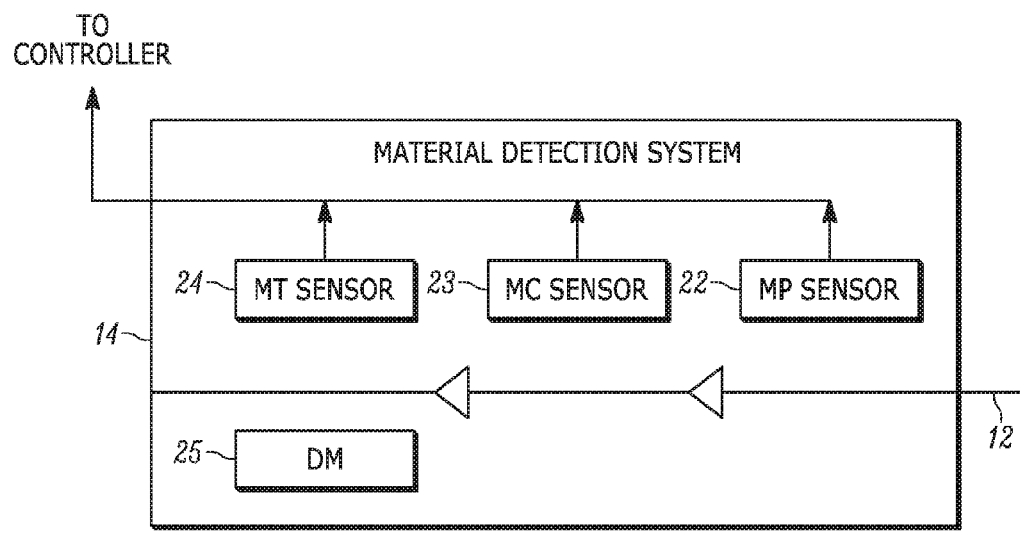
FIG. 2 is a block diagram of an example material detection assembly that is used in the system shown in FIG. 1.
Figure 3:
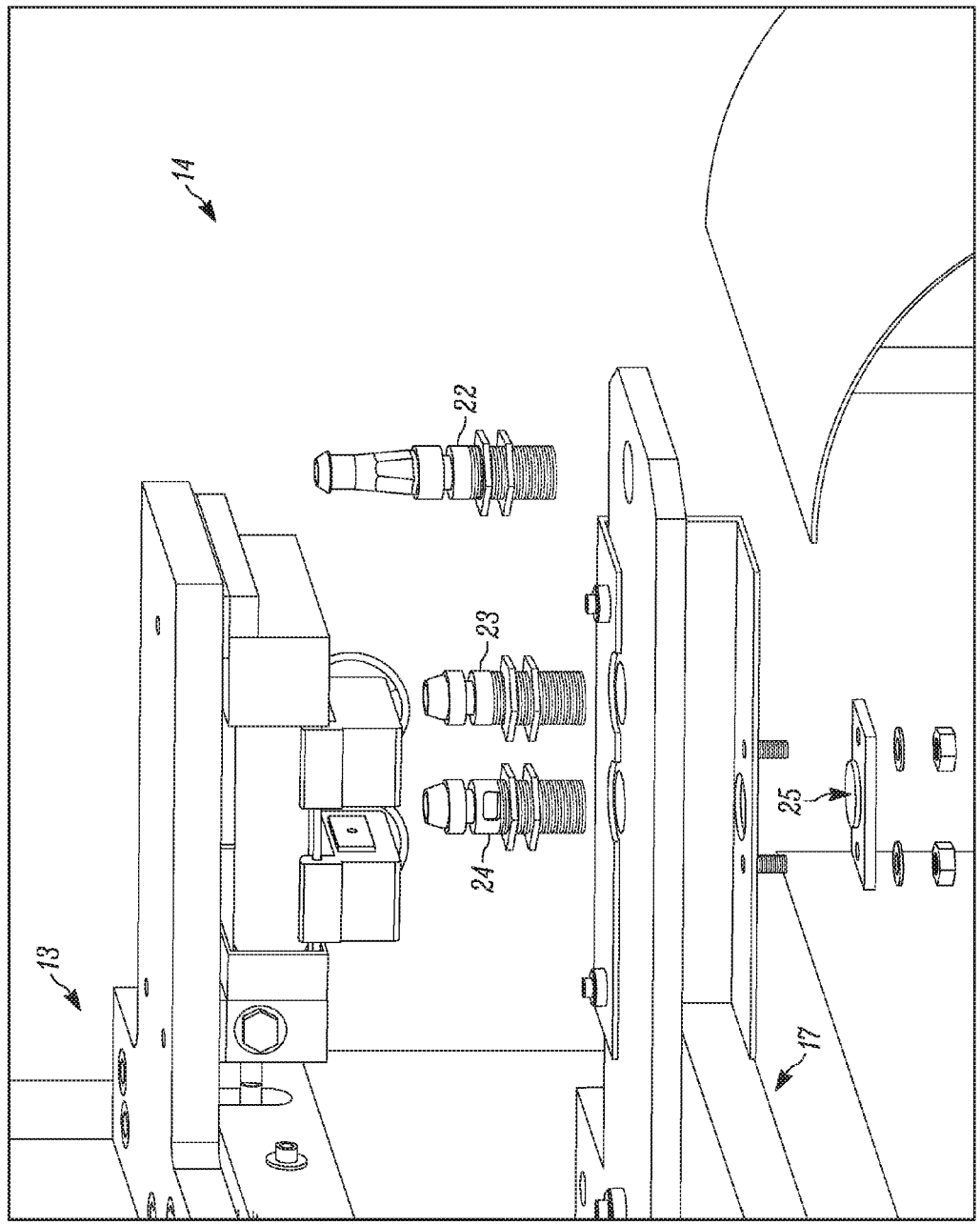
FIG. 3 is an illustration of a partially exploded view of an example material detection assembly used in the system shown in FIG. 1.
Figure 4:
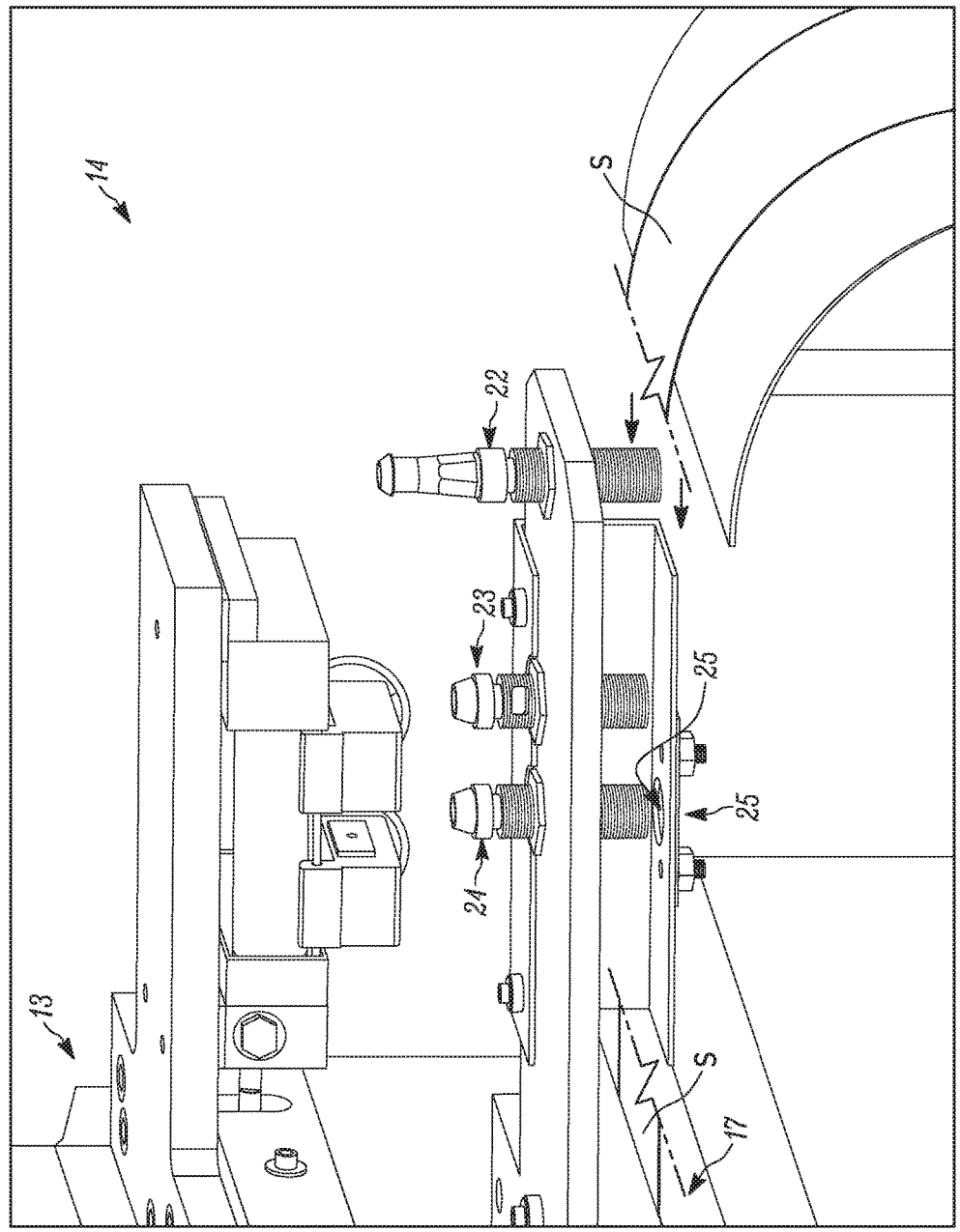
FIG. 4 is an illustration of a partially assembled example material detection assembly used in the system shown in FIG. 1 wherein a material is partially omitted.
Figure 5:
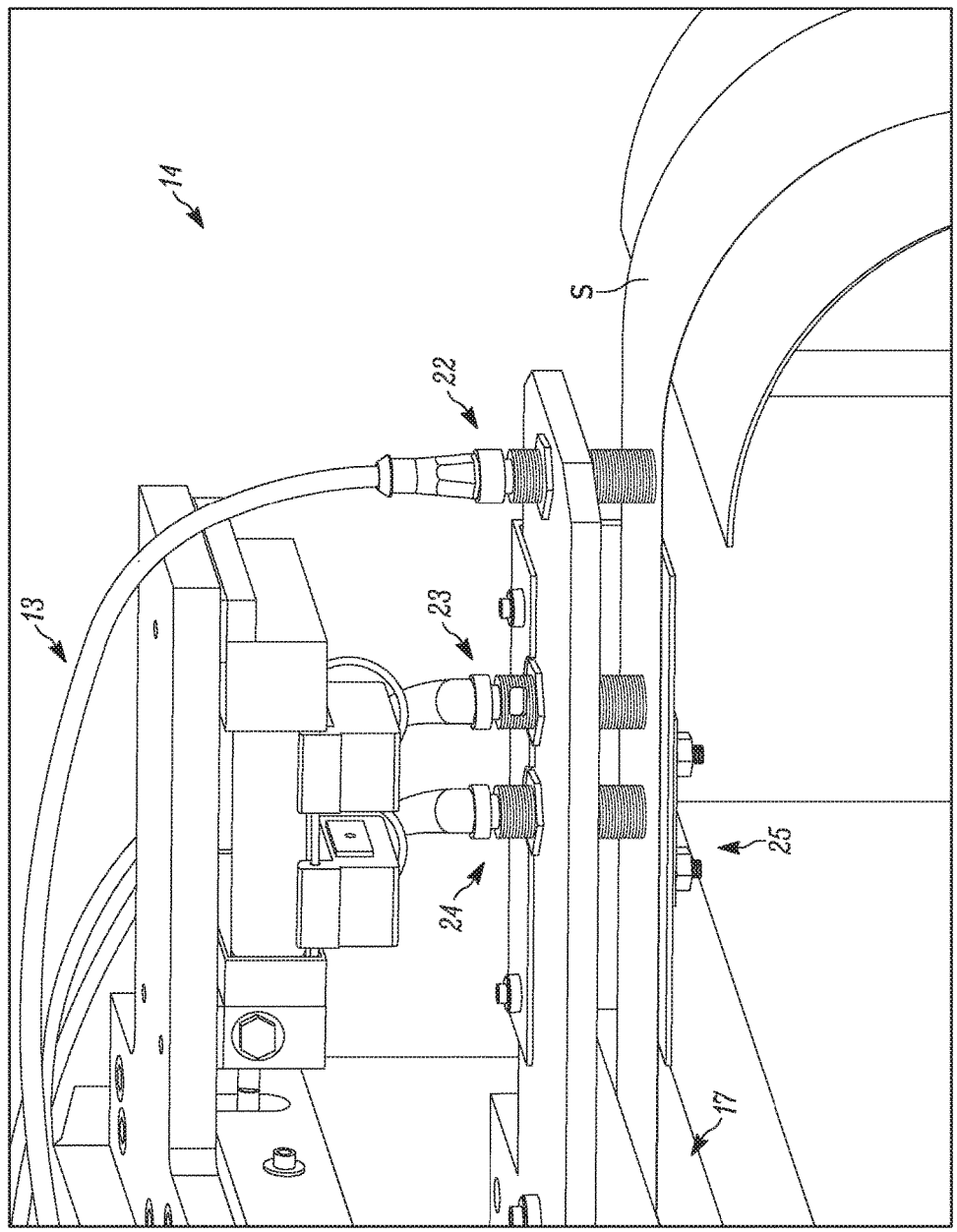
FIG. 5 is an illustration of an assembled example material detection assembly used in the system shown in FIG. 1.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of the example embodiments of the present disclosure.

The apparatus, system, and method components have been represented where appropriate by conventional symbols in the drawings, showing only those specific details that are pertinent to understanding the example embodiments of the present disclosure so as not to obscure the disclosure with details that will be readily apparent to those of ordinary skill in the art having the benefit of the description herein.

DETAILED DESCRIPTION

Referring now to the figures generally wherein like numbered features shown therein refer to like elements having similar characteristics and operational properties throughout unless otherwise noted. The present disclosure relates to a material detection system that can be employed by a controller to determine type of material at a machine input to prevent damage to the machine, or allow the changes to occur to the machine or subsequent equipment based on the determination.

Illustrated in FIG. 1 is a material detection system 10 constructed in accordance with one example embodiment of the present disclosure. In the illustrated example embodiment, the material detection system 10 comprises a material detection assembly 14 and a controller 15. The material detection assembly 14 is located at or near an input 17 to a machine 13 and includes a plurality of sensors 22, 23, 24 to detect a presence of a material 12 at the input 17 of the machine 13 and to detect properties of the material 12. The controller 15 of the machine 13 (e.g., a programmable logic controller (PLC) or similar device) adjusts at least one parameter of the machine based on a type of the material 12 determined based on at least a portion of the detected properties of the material to prevent damage to the machine 13, and/or allow for changes to occur to the machine or subsequent equipment based on the determination. Stated another way, if the type of material 12 to be processed by the machine 13 is different in the type or grade (type of material and thickness or hardness, respectively) than what the machine is currently setup to run and/or process, the controller 15 adjusts the machine to run the detected material without damage to the machine and/or to increase processing time.

Figure 12:
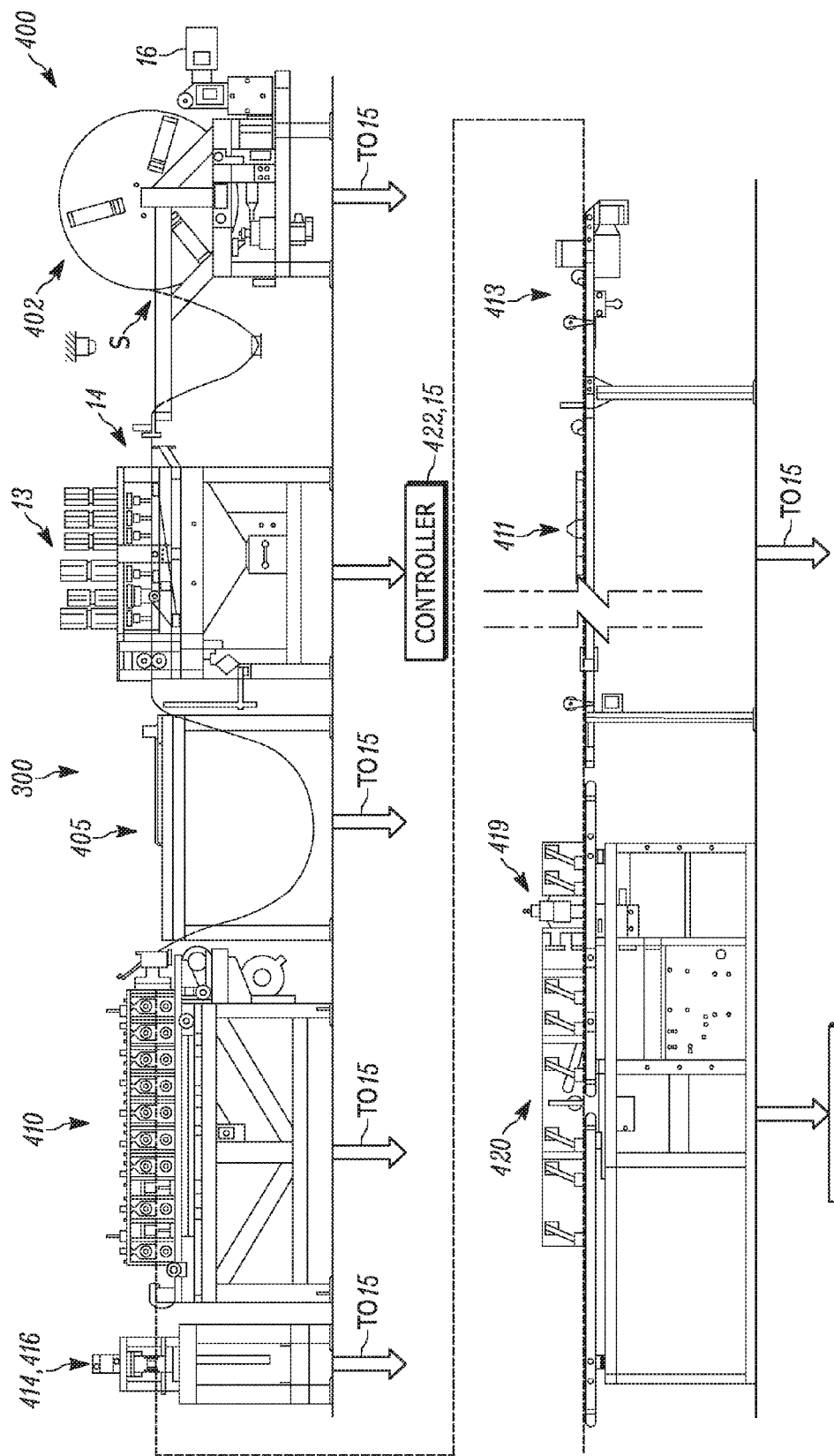
FIG. 12 illustrates equipment in an assembly line for making a spacer frame.

In one example embodiment, the change to the machine 13 by the controller 15 occurs via a feedback loop 15a and 15b. The feedback loop 15a, 15b provides information from the detection assembly 14 and provides it to the machine 13. In FIG. 12, the machine 13 is found to be any part of an assembly line 400 of additional equipment 402-420. However, in the illustrated example embodiment, the machine 14 is a crimping/punching station. The assembly line 400, machine 13, and its equipment 402-420 are used to make the spacer frame for an IGU from coil stock S. The process of making the spacer frame for an IGU, the details of the spacer frame, and operation of the equipment is further discussed in U.S. Pat. No. 9,212,515, which is incorporated by reference. In one example embodiment, the assembly line 400 is fed sheet metal stock endwise from the coil stock S into one end of the assembly line and substantially completed elongated window components, e.g., the spacer frame emerges from the other end of the line 400.

The line 400 comprises a stock supply station 402, the machine 13, a transfer mechanism 405, a first forming station 410, second and third forming stations 414, 416, a conveyor 413, and a scrap removal apparatus 411, respectively, where partially formed spacer frames are separated from the leading end of the stock and frame corner locations are deformed preparatory to being folded into their final configurations, a desiccant application station 419 where desiccant is applied to an interior region of the spacer frame, and an extrusion station 420 where sealant is applied to the yet to be folded spacer frame. A scheduler/motion controller unit 15, 422 interacts with the stations and loop feed sensors and the sensors 22, 23, 24 to at least one of govern a spacer stock size, a spacer assembly size, stock feeding speeds in the line, and other parameters involved in production of a window or door spacer frame. A preferred controller unit 15, 422 is commercially available from Delta Tau, 21314 Lassen St, Chatsworth, Calif. 91311 as part number UMAC, while it would be appreciated by one of ordinary skill in the art that other types/brands of controllers, CPUs, and/or PLCs could be used.

In an example shown in FIGS. 2-5, the material detection assembly 14 comprises three different sensors: a material present (MP) sensor 22, a material color (MC) sensor 23, and a material type (MT) sensor 24, Although the material detection assembly 14 shown in FIGS. 2-5 are configured with the sensors arranged so that the material 12 first encounters the MP sensor 22, then the MC sensor 23, and then the MT sensor 24, it will be apparent that the MC sensor 23 and the MT sensor 24 may be arranged in any order, as long as material 12 encounters the MP sensor 22 first.

The sensors 22-24 of the material detection system 14 can each detect a different property of the material 12. In one example, the material 12 can be a thin gauge material (or metal strip "S") used in the fabrication of spacer assemblies for IGUs, such as standard thinplate steel (mild tin plated steel), black thinplate steel (mild tin plated steel painted black), ultra stainless steel, galvanized steel, aluminum copper, brass, or black ultra stainless steel (stainless steel painted black). If not properly configured for the material 12, machine tooling or other parts of the machine 13 and/or equipment 402-420 that are sensitive to the type the material 12, may break if improperly configured, leaving the machine 13 and equipment 402-420 operating at a reduced efficiency or unable to fabricate spacer, assemblies correctly, disrupting the window or door-making process.

The MP sensor 22 detects a presence of the material 12 at the input 17 to the machine 13 (detecting whether or not the material 12 is loaded in the machine 13). In one example embodiment, the MP sensor 22 includes an inductive proximity sensor (e.g., one commercial embodiment includes an IFM Efector sensor part no. IGC224, manufactured by IFM Efector, Inc., Malvern, Pa.) that is capable of detecting the presence of all metals within a sensing range. The sensing range of the inductive proximity sensor can be expressed as follows:

Sensing Range=(Nominal Sensing Range)*(Correction Factor)   Equation 1

As shown in Equation 1, the sensing range is variable based on correction factors for different metals listed in Table 1.

TABLE 1

Correction factors for different materials.

| Material | Approximate Correction Factor |
| --- | --- |
| Mild Steel | 1.0 |
| Stainless Steel | 0.85 |
| Brass | 0.50 |
| Aluminum | 0.45 |
| Copper | 0.40 |

The MC sensor 23 detects a degree of absorbency or reflectivity of the material 12. In one example embodiment, the MC sensor 23 includes an adjustable diffuse reflective photoelectric sensor (e.g., one commercial embodiment includes an IFM Efector part no. OGT204, manufactured by IFM Efector, Inc., Malvern, Pa.) that transmits a beam of light onto the material 12 and measures an amount or an intensity of light that is reflected back to the sensor. Accordingly, the MC sensor 23 is able to detect a difference in contrast of between different types of material. For example, the MC sensor 23 can detect materials that are black and materials that are not black with a high degree of accuracy. Stated another way, a black surface will have a reflectivity closer to 0% and an unpainted reflective surface will reflectivity closer to 100% of visible light. The point at which the MC sensor 23 transitions between the 0% to 100% state is adjustable based upon the MC sensor's sensitivity setting. As the differential between black and not black in reflected light is large, the MC sensor 23 identifies black and not black with a high degree of accuracy. The information detected by the MC sensor 23 can be used to distinguish between standard thinplate steel and black thinplate steel or ultra stainless steel and black ultra stainless steel, since each has a different surface contrast.

The MT sensor 24 detects a type of the material 12. For example, the MP sensor 24 includes a Ferrous only inductive sensor (e.g., an IFM Efector #IGC 249, IFM Efector, Inc., Malvern, Pa.), which can determine a difference between mild steel (e.g., thinplate steel) and stainless steel. As a Ferrous only sensor, the MT sensor 24 is immune to sensing metals with correction factors of about 0.5 or less (shown in Table 1). However, the MT sensor 24 is generally unable to differentiate between ferrous steel and stainless steel with a high degree of accuracy. By placing a different material (DM) 25 with a correction factor less than or equal to 0.5 opposed to the MT sensor 24, the MT sensor 24 becomes able to differentiate between mild steel and stainless steel with a high degree of accuracy. As an example, the MT sensor 24 and the DM 25 can be arranged so that the material 12 is placed between the MT sensor 24 and the DM 25.

The DM can be any material with a correction factor less than or equal to 0.5, like brass, aluminum, and copper. The material can be configured, for example, in the shape of a block or a cylinder or any other shape that allows the DM 25 to be placed in a position opposed to the MT sensor 24. As an example, the DM 25 is an aluminum block or an aluminum cylinder. In this example, the MT sensor 24 distinguishes between ferrous steel and stainless steel based on a magnetic field absorbed or not absorbed by the material 12. Ferrous steel absorbs a magnetic field, while stainless steel does not absorb the magnetic field. The aluminum DM 25 located behind the material 12 is able to shunt or not shunt the magnetic field, which enables the MT sensor 24 to determine the difference between ferrous steel and stainless steel in the strip S.

The sensors 22-24 deliver signals to the controller 15 included the respective detected property. For example, the MP sensor 22 delivers a signal to the controller 15 indicating whether the material 12 is present at the input 17 to the machine 13. The MC sensor 23 delivers a signal to the controller 15 indicating the degree of absorbency or reflectivity of the material 12. The MT sensor 24 delivers a signal to the controller indicating a degree of iron or magnetism of the material 12. The controller 15 determines the type of material (e.g., copper, steel, etc.) and grade of the material (e.g., thickness and/or hardness of the material) based on the signals received from the sensors 22-24 to ensure that the machine 13 is properly configured for the material 12. In one example embodiment, the controller 15 determines whether the material 12 is standard thinplate steel (mild tin plated steel), black thinplate steel (mild tin plated steel painted black), ultra stainless steel, black ultra stainless steel (stainless steel painted black), copper, aluminum, or brass based on the properties detected by the sensors 22-24. The controller 15 can include safe parameters related to the type of the material that can be used to ensure that the machine 13 and equipment 402-420 is properly configured for the material 12.

Figure 6:
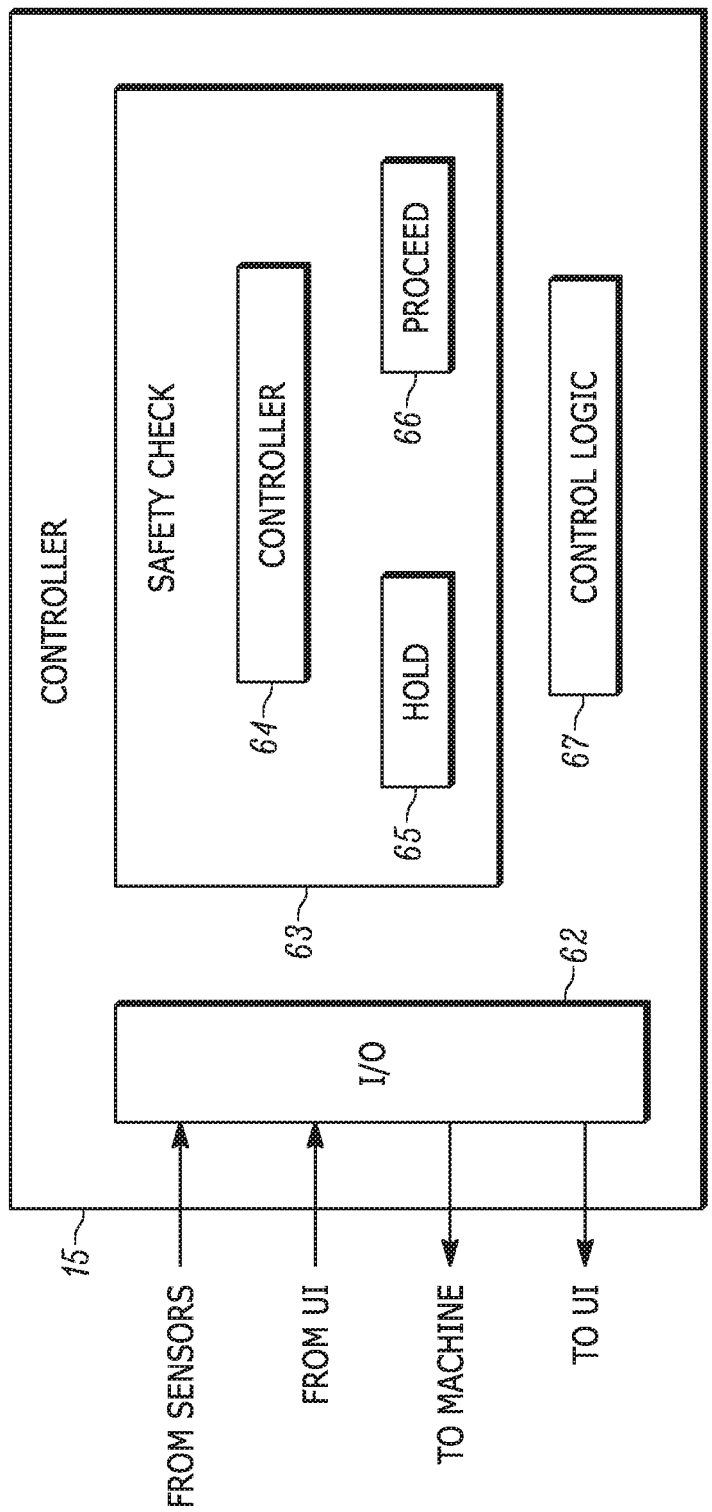
FIG. 6 is a block diagram of an example controller used in the system shown in FIG. 1.

An example of the controller 15 is shown in FIG. 6. The controller 15 contains control logic 67 that includes a safety check 63 before allowing the machine 13 to run. The safety check 63 may prevent the machine 13 from running while configured for the wrong material. The signals from the sensors 22-24 are used as feedback related to the material that is loaded into the machine 13 for the safety check 63 to perform its comparison of the material 12 to the configuration of the control logic 67.

Figure 7:
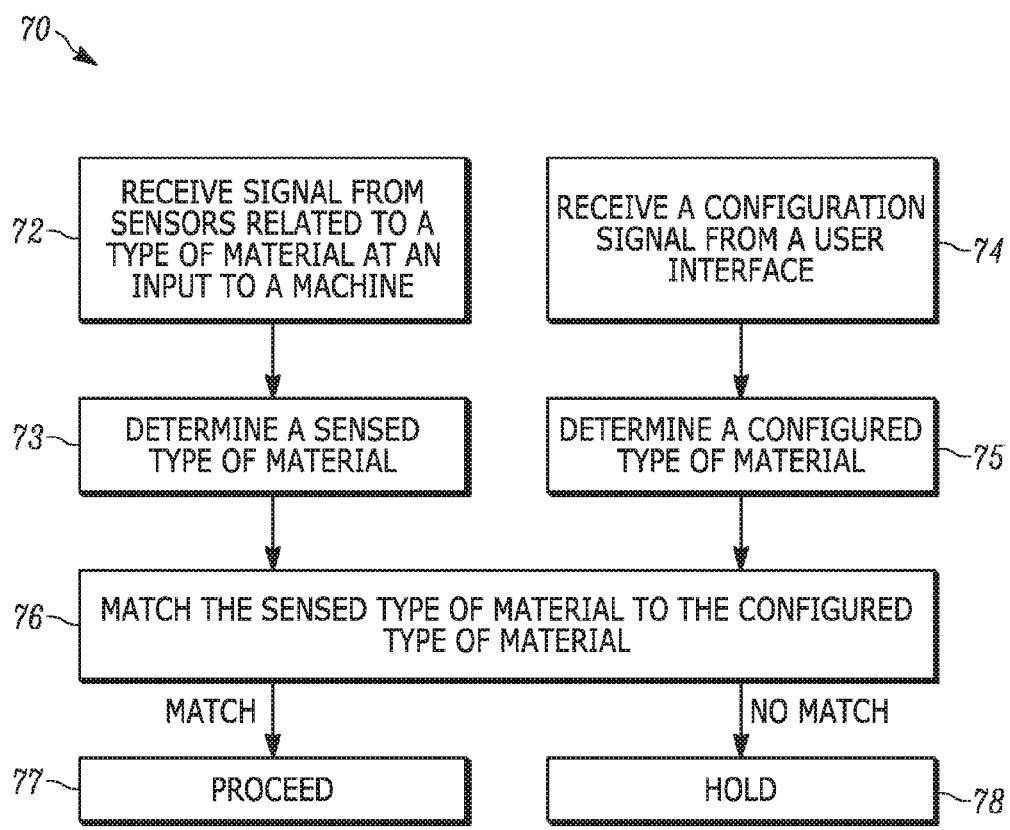
FIG. 7 is a process flow diagram of an example method for facilitating the operation of a machine based on determining a material present that can be implemented by the controller shown in FIG. 6.

An example method 70 of operation of the safety check 63 of the controller 5 is shown in FIG. 7. At 72, the controller 15 receives through I/O 62 signals from the sensors 22-24 related to the type of material 12 at the input 17 to the machine 13. From the sensors 22-24, the controller 15 receives information related to the material 12 being present at the input 17 to the machine 13, information related to the degree of absorbency, or reflectivity of the material 12, and information related to the type of the material 12. Using this information, at 73, the controller 15 determines a sensed type of material 12. For example, the sensed type of material 12 can be standard thinplate steel (mild tin plated steel), black thinplate steel (mild tin plated steel painted black), ultra stainless steel, copper, brass, aluminum or black ultra stainless steel (stainless steel painted black) determined based on information from the MC sensor 23 and the MT sensor 24. Through the I/O 62, at 74, the controller 15 receives a configuration signal from the UI 16. This configuration signal is received before, at about the same time, or after the signals are received from the sensors 22-24. At 75, the configured type of material is determined by the controller 15.

At 76, the comparator 64 of the safety check 63 matches the sensed type of material to the configured type of material. If there is a match between the sensed type of material and the configured type of material, at 77, the control logic 67 allows the machine 13 to proceed with the configuration for the material. The controller 15 communicates at least a portion of the control logic 67 configured as is to the machine 13 through the I/O 62 to control operations of the machine 13 and its components. However, if there is not a match between the sensed type of material and the configured type of material, at 78, the control logic 67 allows the controller 15 to hold the process in order for the configuration to be changed. The controller 15 communicates with the UI 16 through the I/O 62 to undertake the reconfiguration for the sensed type of material. After the configuration is changed, the controller 15 communicates at least a portion of the reconfigured control logic 67 to the machine 13.

Figure 8:
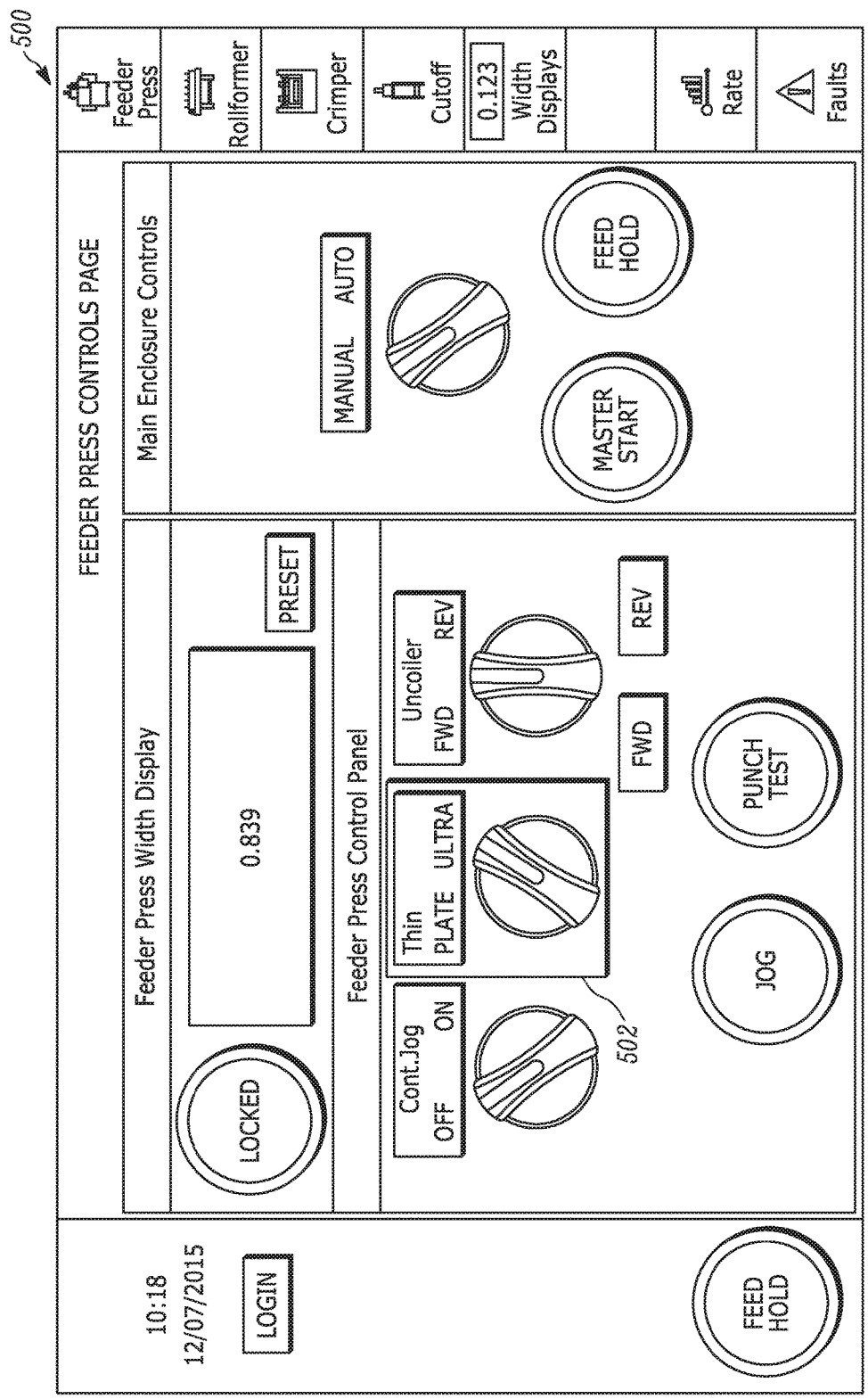
FIG. 8 illustrates a first example user interface screen that can be configured and used by the system shown in FIG. 1.

Different example UIs 16 are shown in FIGS. 8-11. The examples in FIGS. 8-11 correspond to operation of a feeder press. Shown in FIG. 8 is a basic operator interface screen 500 allowing selection of the type of material 12 being loaded into the machine 13. A selector switch 502 is included to select the material. In this example, an operator moves the selector switch 502 to the left or right to the position corresponding to the material 12 to be entered into the machine 13.

Figure 9:
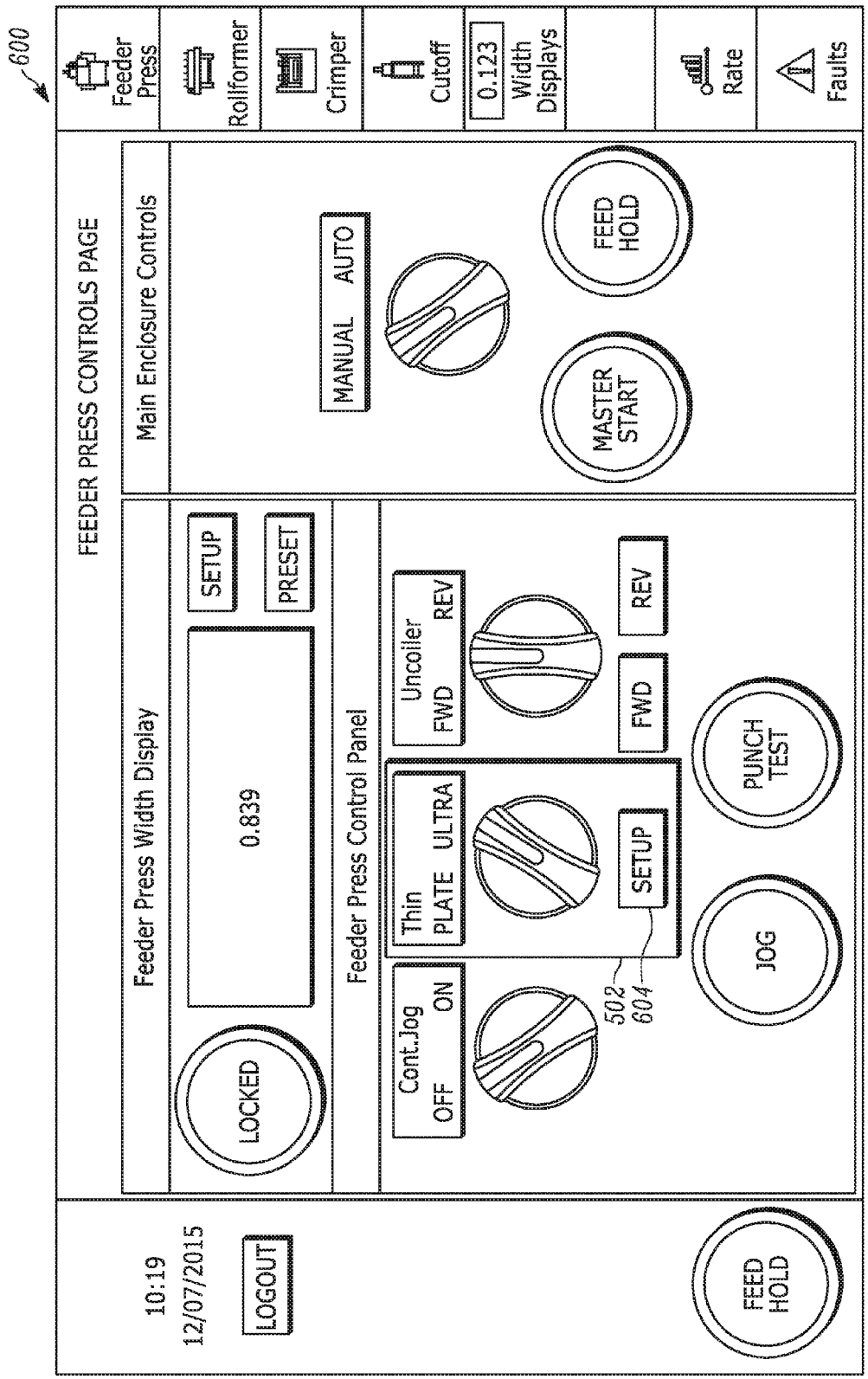
FIG. 9 illustrates a second example user interface screen that can be configured and used by the system shown in FIG. 1.
Figure 10:
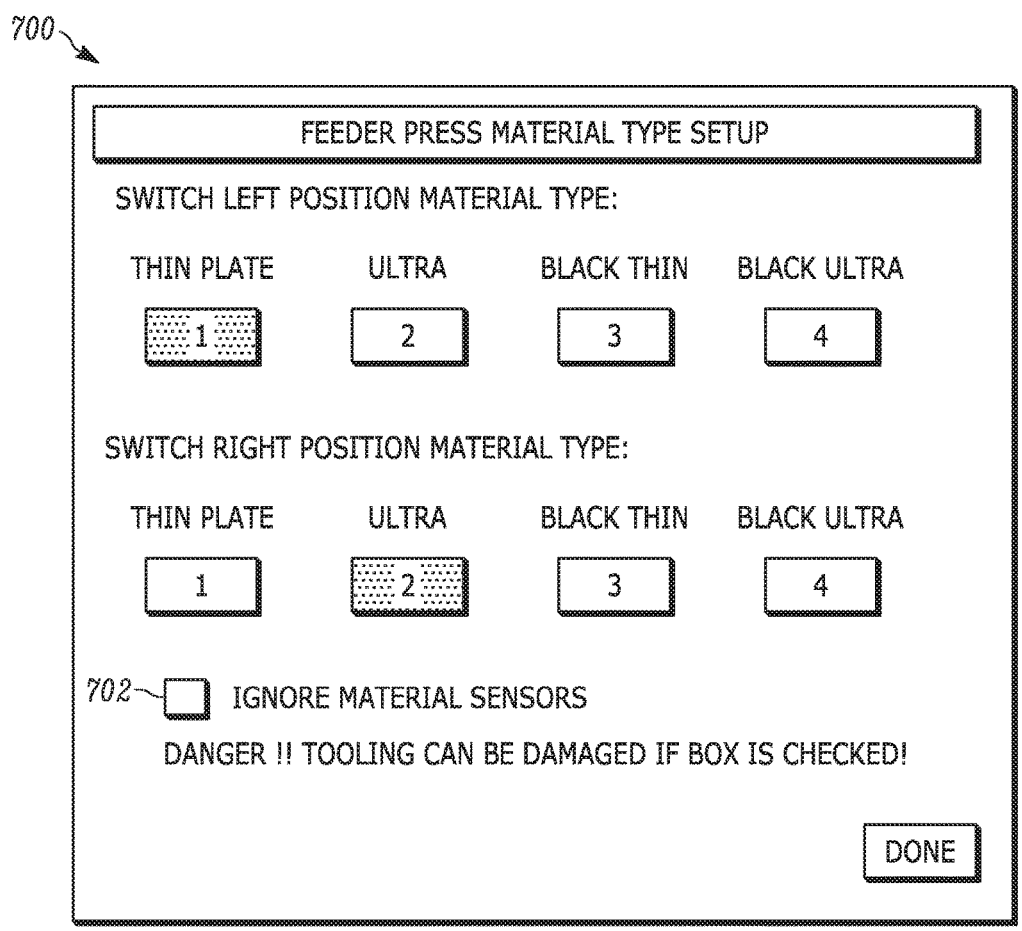
FIG. 10 illustrates a third example user interface screen that can be configured and used by the system shown in FIG. 1.
Figure 11:
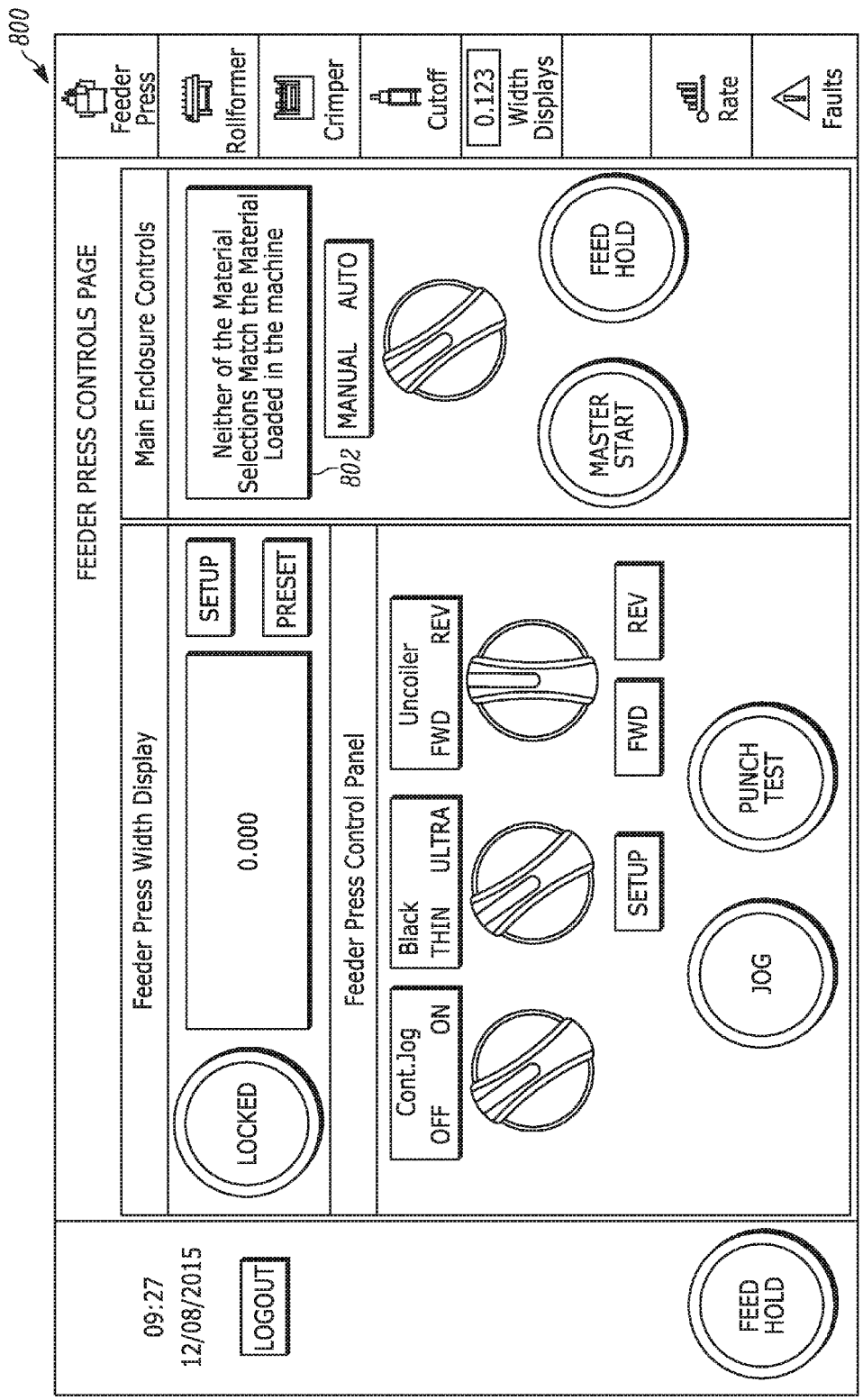
FIG. 11 illustrates a fourth example user interface screen that can be configured and used by the system shown in FIG. 1.

FIG. 9 shows an example of a different user interface 600 seen by someone who logs in as an Administrator. An Administrator has different permissions than a general operator such that the Administrator reconfigures the UI. For example, the different user interface 600 will display a setup button 604 in connection with the selector switch 502 such that when the setup button is pressed, another operator interface screen 700 shown in FIG. 10 appears that allows the Administrator to select a number of materials (e.g., two) to appear on the operator interface screen 500 of FIG. 8. The materials selected should ultimately match the configuration of the machine 13. For example, die stops that are installed on quick change platens indicate materials that can be used on the machine 13 without damaging the machine. The operator interface 700 of FIG. 10 also includes a check box 702 telling the controller 15 to ignore the inputs from the sensors 22-24. For example, the Administrator could check this box in the event that one or more of the materials sensors were to go bad and the machine 13 was still desirous to run the machine. FIG. 11 shows an example of an operator interface 800 that is automatically updated with the two materials that are selected by the Administrator. If either of the two material selections fails to match the material 12 that is loaded into the machine 13, a message 802 appears in the top right corner of the operator interface screen 800 (see FIG. 11) alerting the user of the operator interface and/or the person who loaded the material into the machine. When the message 802 appears on the operator interface screen 800, the machine 13 will also be prevented from running in AUTO mode unless the "ignore material sensors" checkbox 702 is checked or the material type selector is updated to reflect what is actually in the machine 13.

In yet another example, a material type will be predetermined via a schedule that is downloaded onto the controller 15, rather than being manually selected as indicated in FIGS. 8-11. In an example embodiment, the schedule is downloaded via a communication port (e.g., a USB port, a signal transceiver, a signal receiver, or the like).

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A system comprising:
   a material detection system to detect a presence of a material during use at an input to a machine and to detect properties of the material, the material detection system comprising:
      a material present sensor;
      a material type sensor opposed by a different material having an inductive sensor correction factor of 0.5 or less; and
      a material color sensor; and
   a controller of the machine to adjust at least one parameter of the machine based on a type of the material determined based on the properties of the material to prevent damage to the machine wherein the material during use is placed between the material type sensor and the different material.

2. The system of claim 1, wherein the material present sensor comprises an inductive proximity sensor configured to detect the presence of a metal material at the input to the machine.

3. The system of claim 1, wherein the material during use comprises a metal material, wherein the different material allows the material type sensor to discriminate between a mild steel of the metal material and a stainless steel of the metal material.

4. The system of claim 1, wherein the material type sensor is immune to sensing metals with an inductive sensor correction factor of 0.5 or less.

5. The system of claim 1, wherein the material type sensor detects a portion of a magnetic field not absorbed by the material.

6. The system of claim 1, wherein the different material comprises at least one of brass, aluminum, and copper.

7. The system of claim 1, wherein the different material is in a shape of a block or a cylinder.

8. The system of claim 1, wherein the material color sensor comprises a diffuse reflective photoelectric sensor that determines at least one of a degree of absorbency and a degree of reflectivity of the material.

9. The system of claim 1, wherein the controller determines the type and grade of the material based on signals received from the material present sensor, the material type sensor, and the material color sensor.

10. The system of claim 1, wherein the controller compares safe parameters related to the type of material to a material selected based on an input to a graphical user interface to allow for an automated change over to prevent damage to the machine.

11. The system of claim 1 further comprising:
    at least one of a user interface and communication port that receives a selection of the type of material to be loaded into the machine; and
    said controller that performs a safety check matching the selected material type to a material type determined based on signals received from the plurality of sensors comprising the material present sensor, the material type sensor opposed by the different material, and the material color sensor.

12. The system of claim 11, wherein a material detected by the material present sensor is a metal material.

13. A method of detecting a type and grade of material to be processed by a machine, the method comprising the steps of:
    providing a material present sensor;
    providing a material type sensor opposed by a different material having an inductive sensor correction factor of 0.5 or less;
    providing a material color sensor;
    providing a controller in the machine having a feedback loop to adjust at least one parameter of the machine based in the type of material detected; and
    providing a material between the material type sensor and the different material to be identified.

14. The method of claim 13, further comprising the steps of:
    providing an inductive proximity sensor configured to detect the presence of a metal material at the input to the machine.

15. The method of claim 13, further comprising the steps of:
    providing a diffuse reflective photoelectric sensor that determines a contrast of the material.

16. The method of claim 13, further comprising the steps of:
    determining the type and grade of the material based upon signals received from the material type sensor and the material color sensor.

17. The method of claim 13, further comprising the steps of:
    providing at least one of brass, aluminum, and copper to comprise the different material.

18. The method of claim 13, further comprising the steps of:
    detecting a portion of a magnetic field not absorbed by the material to determine the material type.

19. The method of claim 13, further comprising the steps of:
    comparing safe parameters related to the type of material detected by the sensors to a material selected based on the selection of a material type to allow for a change over to prevent damage to the machine.

20. A system comprising:
a material detection system to detect a presence of a material during use at an input to a machine and to detect properties of the material, the material detection system comprising:
  a material present sensor comprising an inductive proximity sensor;
  a material type sensor opposed by a different material having an inductive sensor correction factor of 0.5 or less, wherein the material type sensor detects a portion of a magnetic field not absorbed by the material, wherein the material during use is placed between the material type sensor and the different material; and
  a material color sensor comprising a diffuse reflective photoelectric sensor that determines at least one of a degree of absorbency and reflectivity of the material; and
a controller of the machine that includes a feedback loop to the machine, which performs a safety check matching a selected material type to a material type determined based on signals received from the sensors and based upon a prior and different material processed by said machine during use, said controller adjusts at least one parameter of the machine based on a type of a subsequent material determined based on the properties of the subsequent material to prevent damage to the machine.

* * * * *